United States Patent
Bello et al.

(10) Patent No.: US 10,027,179 B1
(45) Date of Patent: Jul. 17, 2018

(54) CONTINUOUS WIRELESS POWERING OF MOVING BIOLOGICAL SENSORS

(71) Applicants: Simon Antonio Bello, Tampa, FL (US); Christopher L. Passaglia, Lutz, FL (US)

(72) Inventors: Simon Antonio Bello, Tampa, FL (US); Christopher L. Passaglia, Lutz, FL (US)

(73) Assignee: University of South Florida, Tampa, FL (US)

( * ) Notice: Subject to any disclaimer, the term of this patent is extended or adjusted under 35 U.S.C. 154(b) by 236 days.

(21) Appl. No.: 15/144,304

(22) Filed: May 2, 2016

Related U.S. Application Data

(60) Provisional application No. 62/155,152, filed on Apr. 30, 2015.

(51) Int. Cl.
| | |
|---|---|
| H01F 27/42 | (2006.01) |
| H01F 37/00 | (2006.01) |
| H01F 38/00 | (2006.01) |
| H02J 50/23 | (2016.01) |
| H02J 50/40 | (2016.01) |
| H02J 50/80 | (2016.01) |
| A61B 5/07 | (2006.01) |

(52) U.S. Cl.
CPC .............. *H02J 50/23* (2016.02); *A61B 5/076* (2013.01); *H02J 50/40* (2016.02); *H02J 50/80* (2016.02); *A61B 2560/0209* (2013.01); *A61B 2560/0219* (2013.01)

(58) Field of Classification Search
USPC ........................................................ 307/104
See application file for complete search history.

(56) References Cited

U.S. PATENT DOCUMENTS

| | | | |
|---|---|---|---|
| 6,579,235 B1 | 6/2003 | Abita et al. | |
| 7,131,945 B2 | 11/2006 | Fink et al. | |
| 8,753,305 B2 | 6/2014 | Field et al. | |
| 2006/0025897 A1* | 2/2006 | Shostak | ............... B60C 23/005 701/1 |
| 2010/0161004 A1 | 6/2010 | Najafi et al. | |
| 2011/0074349 A1 | 3/2011 | Ghovanloo | |

(Continued)

FOREIGN PATENT DOCUMENTS

WO 2014027306 A3 2/2014

OTHER PUBLICATIONS

Shih, Yi-Chun, et al., A 2.3 uW Wireless Intraocular Pressure/Temperature Monitor. IEEE Journal of Solid-State Circuits, vol. 46, No. 11, Nov. 2011. pp. 2592-2601.

(Continued)

*Primary Examiner* — Adam Houston
(74) *Attorney, Agent, or Firm* — Michele L. Lawson; Smith & Hopen, P.A.

(57) ABSTRACT

A system and method for continuous wireless monitoring and powering of at least one sensor is presented. The system is generally comprised of at least one sensor, at least one RF transmitter, an energy harvester, an energy storage unit, a microprocessor and a receiving antenna. Multiple RF transmitters may be positioned in an orthogonal orientation within reach of the receiving antennae to provide equally strong RF fields. The system may additionally include metal shielding around the area in which the system is operating.

18 Claims, 11 Drawing Sheets

(56) References Cited

U.S. PATENT DOCUMENTS

| | | | |
|---|---|---|---|
| 2011/0181399 A1* | 7/2011 | Pollack | G06K 19/0707 340/10.33 |
| 2014/0335490 A1* | 11/2014 | Baarman | A61B 5/002 434/236 |
| 2015/0287544 A1* | 10/2015 | Irazoqui | H01G 11/36 361/502 |
| 2016/0125276 A1* | 5/2016 | Spicola, Sr. | A01K 11/008 382/110 |
| 2016/0261031 A1* | 9/2016 | Dion | H01Q 1/248 |
| 2017/0070079 A1* | 3/2017 | Manova-Elssibony | H02J 7/025 |
| 2017/0085120 A1* | 3/2017 | Leabman | H02J 7/042 |
| 2017/0208597 A1* | 7/2017 | Gollakota | H04W 72/0473 |
| 2017/0222471 A1* | 8/2017 | Kim | H02J 17/00 |
| 2017/0228626 A1* | 8/2017 | Nikunen | G06K 17/0022 |
| 2017/0249542 A1* | 8/2017 | Gabriel | G06K 19/0707 |
| 2017/0258585 A1* | 9/2017 | Marquez | A61F 2/2409 |
| 2017/0302109 A1* | 10/2017 | Lee | H02J 50/10 |
| 2017/0339585 A1* | 11/2017 | Cortes | H04W 24/08 |
| 2017/0373394 A1* | 12/2017 | Blumberg, Jr. | H01Q 1/50 |
| 2018/0025500 A1* | 1/2018 | Nielsen | G06T 7/277 |
| 2018/0048178 A1* | 2/2018 | Leabman | H02J 50/23 |
| 2018/0049300 A1* | 2/2018 | Recker | H05B 37/0218 |
| 2018/0107492 A1* | 4/2018 | Hall | H04L 12/4625 |

OTHER PUBLICATIONS

Mansouri, Kaweh, et al., Continuous Intraocular Pressure Monitoring with a Wireless Ocular Telemetry Sensor: Initial Clinical Experience in Patients with Open Angle Glaucoma. BR. J. Ophthalmol (2010). pp. 1-3.

* cited by examiner

A

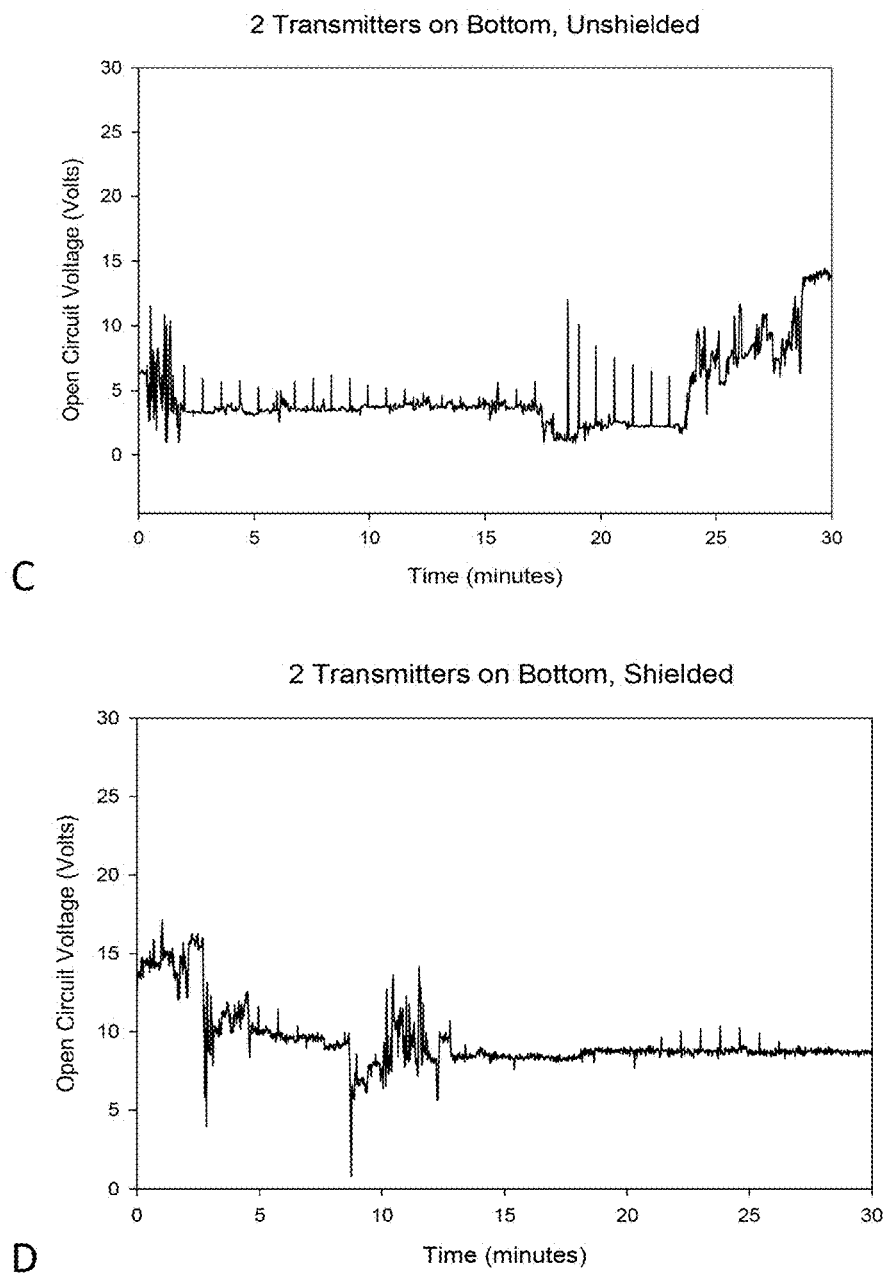
Figure 7C-D

A
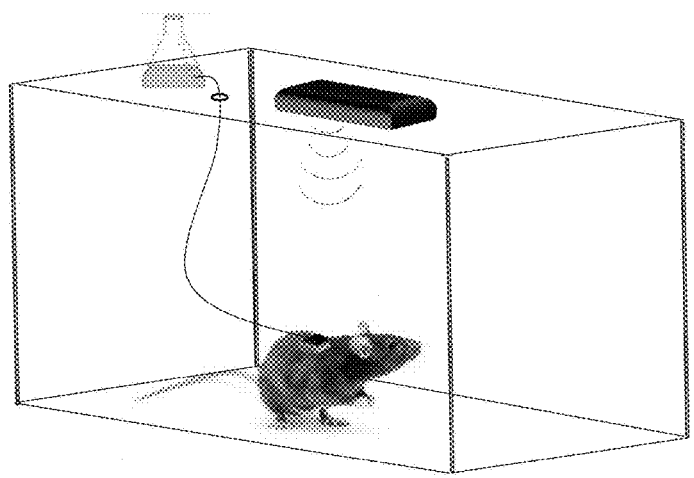
B
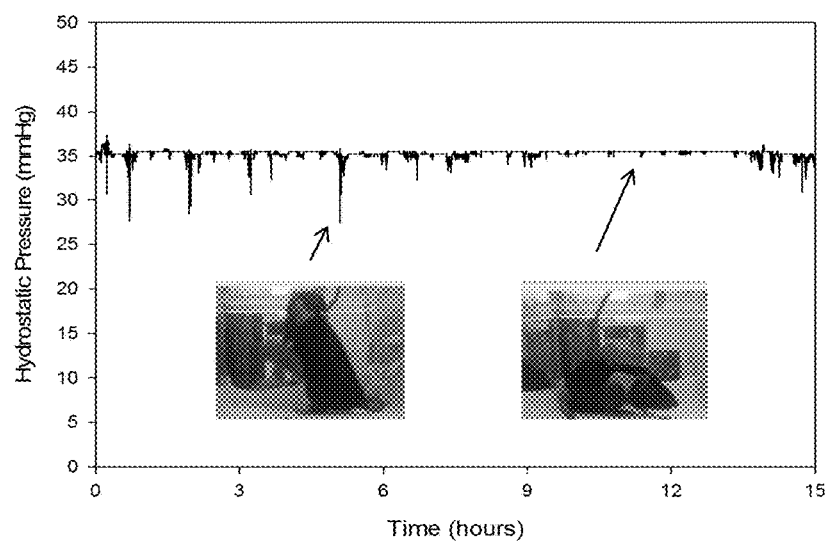
Figure 8A-B

CONTINUOUS WIRELESS POWERING OF MOVING BIOLOGICAL SENSORS

CROSS REFERENCE TO RELATED APPLICATIONS

This application is a nonprovisional of and claims priority to U.S. Provisional Patent Application No. 62/155,152, entitled "Continuous Wireless Powering of Moving Biological Sensors", filed Apr. 30, 2015, the entire contents of each of which is herein incorporated into this disclosure.

GOVERNMENTAL SUPPORT

This invention was made with Government support under Grant No. R21 EY023376 awarded by the National Institutes of Health (NIH). The Government has certain rights in the invention.

FIELD OF INVENTION

This invention relates to a system for wirelessly powering moving biological sensors. Specifically, the invention provides a system employing energy harvesting technology to continuously deliver a constant power supply to sensors.

BACKGROUND OF THE INVENTION

Energy harvesting is a process which captures small amounts of energy that would otherwise be lost as heat, light, sound, vibration or movement. In general, the energy can be stored in a capacitor, super capacitor or battery and the small amounts of energy can be used to power small low-energy electronics such as wireless sensor networks and wearable electronics. The external sources that generate energy include solar power, thermal power, wind power, salinity gradients and kinetic energy.

Radio frequency (RF) energy harvesting can occur to capture RF energy using a power generating circuit linked to a receiving antenna. This RF energy can then be converted into usable DC voltage. In the same way as other energy harvesting sources, the converted power can either be stored directly in a battery, or can be accumulated in a capacitor or supercapacitor to power circuits directly or charge a battery. It is known that the levels of RF energy available drop considerably with distance, following the inverse square law. Devices are typically tuned to operate most efficiently at specific frequencies.

Energy harvesting has been used in the past for powering industrial sensors, however, in these cases both the source and the harvester are fixed in position, allowing for an easier wireless transfer of energy between them. Biological systems, on the other hand, represent an extra challenge due to the fact that the subject has the ability to move freely. These movements create constant alterations in the receiving antenna position, which diminish the ability of harvesting systems to collect energy. Such limitations are amplified by the fact that the subject movements are random and cannot be anticipated in order to create a correction algorithm.

Battery drainage can affect a sensor's performance over time and significantly limit operational lifetime. In the case of biological sensors, which are often implanted, battery replacement can be challenging and often unviable. This creates a need for sensors that can be alternatively powered.

SUMMARY OF INVENTION

The invention is an electronic system for wirelessly powering of electronics on moving objects without the need of batteries. The system uses energy harvesting technology in conjunction with innovative antenna and transmitter designs to allow the user to power multiple moving sensors or other implantable battery-less devices at once. A working prototype of the invention has been developed for animal research applications, where long term studies are necessary. The system can collect data from an animal moving freely around its cage and transmit the data to a receiver without wires or batteries. The system can accommodate multiple types of sensors and can handle any application in which subjects move within a wirelessly powerable area.

In an embodiment, a system for continuous wireless powering is presented comprising: an RF energy harvester; a receiving antennae oriented in a three dimensional configuration attached to the RF energy harvester; at least one RF transmitter positioned around the receiving antennae; an energy storage unit connected to the RF energy harvester; a microprocessor connected to the energy storage unit; and at least one sensor connected to the microprocessor. The microprocessor can transmit data collected from the at least one sensor to a computer which stores and presents the data.

The system may also contain a highly reflective material positioned around an area in which the system operates.

The energy storage unit can be comprised of at least two supercapacitors and a linear voltage regulator where the voltage stored in the at least two supercapacitors is maintained between minimum and maximum operating levels.

The sensor can be a biological and/or an implantable sensor.

In some embodiments, there are at least two RF transmitters which are positioned around the receiving antennae in an orthogonal orientation. The energy output from the energy harvester can be run through a Schottky diode. The receiving antenna can be a dipole wire antenna. A plurality of RF transmitters can also be positioned around the receiving antenna to create multidirectional RF fields.

The microprocessor can be comprised of multiple general purpose channels capable of being configured as input or output channels. The system can be run in an active mode and a sleep mode.

In another embodiment, a method of continuous wireless powering of a device is presented comprising: providing a system for continuous wireless powering running the system by power cycling through two modalities wherein the two modalities are a sleep mode and an active mode; and transmitting data to a computer. In an embodiment, highly reflective material can be positioned around an area in which the system operates.

The system can be comprised of an energy harvester having a receiving antennae oriented in a three dimensional configuration; at least one RF transmitter positioned around the receiving antennae; an energy storage unit connected to the RF energy harvester; a microprocessor connected to the energy storage unit; and at least one sensor connected to the microprocessor.

The device being powered can be at least one sensor, such as a biological sensor.

There can be at least two RF transmitters positioned around the receiving antennae in an orthogonal orientation.

The energy storage unit is comprised of at least two supercapacitors and a linear voltage regulator.

BRIEF DESCRIPTION OF THE DRAWINGS

For a fuller understanding of the invention, reference should be made to the following detailed description, taken in connection with the accompanying drawings, in which:

FIG. 7C-D is a series of graphs depicting RF-DC mapping around the cage with the system on a fully awake rat. C) Several transmitter positions were explored, with the system mounted on a fully awake rat while the voltage field was monitored as the animal moved. D) Illustrates the effect of adding reflective shielding to the system. An increase of 5 Volts is experienced by the system when metal shielding is added.

FIG. 8A-B is a series of images depicting hydrostatic pressure measurement and recharge cycle with the system mounted on a rat. A) Experimental set up. A beaker with water connected to the pressure transducer applies constant hydrostatic pressure to the system. B) Pressure data wirelessly collected. Large changes in the rat posture (e.g. standing vs. laying down) can create artificial changes in pressure readings, as shown by the arrows. These artifacts will disappear once the system is connected to the eye since the distance between the source (e.g. eye) and the sensor will remain constant.

DETAILED DESCRIPTION OF THE PREFERRED EMBODIMENT

Figure 1:
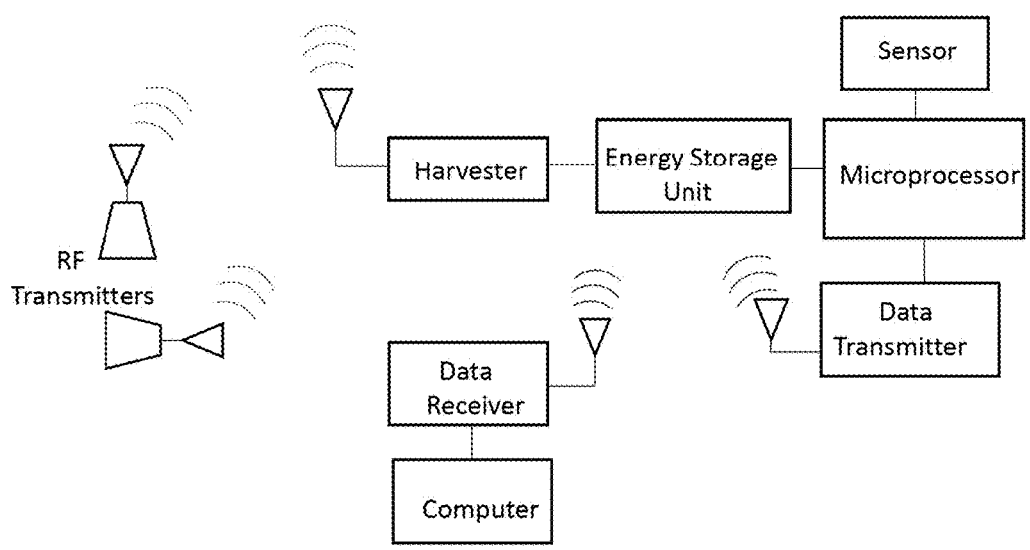
FIG. 1 is an image depicting the system's block diagram. Two transmitters with energy fields that are orthogonal to each other are placed outside the animal's cage. A device harvests the RF energy received and sends it to the storage unit. The energy is used to power a sensor, a microprocessor and a data transmission system. The data collected is then sent to a received for its display and storage in a computer.

In the following detailed description of the preferred embodiments, reference is made to the accompanying drawings, which form a part hereof, and within which are shown by way of illustration specific embodiments by which the invention may be practiced. It is to be understood that other embodiments by which the invention may be practiced. It is to be understood that other embodiments may be utilized and structural changes may be made without departing from the scope of the invention.

Definitions

Unless otherwise defined, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are described herein. All publications mentioned herein are incorporated herein by reference in their entirety to disclose and describe the methods and/or materials in connection with which the publications are cited. It is understood that the present disclosure supercedes any disclosure of an incorporated publication to the extent there is a contradiction.

All numerical designations, such as pH, temperature, time, concentration, and molecular weight, including ranges, are approximations which are varied up or down by increments of 1.0 or 0.1, as appropriate. It is to be understood, even if it is not always explicitly stated that all numerical designations are preceded by the term "about". It is also to be understood, even if it is not always explicitly stated, that the reagents described herein are merely exemplary and that equivalents of such are known in the art and can be substituted for the reagents explicitly stated herein.

Where a range of values is provided, it is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed in the invention. The upper and lower limits of these smaller ranges may independently be excluded or included within the range. Each range where either, neither, or both limits are included in the smaller ranges are also encompassed by the invention, subject to any specifically excluded limit in the stated range. Where the stated range includes one or both of the limits, ranges excluding either or both of those excluded limits are also included in the invention.

The term "about" as used herein refers to being within an acceptable error range for the particular value as determined by one of ordinary skill in the art, which will depend in part on how the value is measured or determined, i.e. the limitations of the measurement system, i.e. the degree of precision required for a particular purpose. In general, the term "about" refers to being approximately or nearly and in the context of a numerical value or range set forth means±15% of the numerical value.

As used in the specification and claims, the singular form "a", "an" and "the" include plural references unless the context clearly dictates otherwise.

"Subject" is used to describe an animal, preferably a mammal, who is confined within an enclosed space. In some embodiments, this enclosed space may be a cage, box, room, building, etc. The enclosed space may be of any size and dimension as long as transmitters are capable of being mounted at the perimeter of the enclosed space.

"Energy transmitter" as used herein refers to a device that receives energy from an energy source and moves (transmits) that energy to another location. The energy received can be a signal or data. In some embodiments, the energy transmitter is used in conjunction with at least one antenna to transmit a radio frequency signal over airwaves (radio wave). These radio waves are used for communication purposes with at least one sensor.

"Energy harvester" as used herein refers to a device which converts energy from one form to another. In some embodiments, the energy harvester captures and converts RF energy to DC power. An RF energy harvester should be able to maintain RF-to-DC conversion efficiency over a wide range of operating conditions, including variations of input power and output load resistance. The energy harvester receives the RF energy from the RF transmitter.

"Energy storage unit" as used herein refers to a device which is used to store energy for use at a later time. The type of energy storage unit used is dependent on the type of energy to be stored. In the case of radiant energy such as RF energy, the energy storage unit includes, but is not limited to, batteries, capacitors and supercapacitors. In some embodiments the energy storage unit is at least one supercapacitor. The at least one supercapacitor can be used in conjunction with a linear voltage regulator in some embodiments.

"Receiving antenna" as used herein refers to an electrical device which converts radio waves into electrical power and vice versa. In some embodiments, the antenna is a dipole wire antenna that is attached to the energy harvester. The length of each of the poles of the antenna is dependent on the frequency used for harvesting.

"Sensor" as used herein refers to a device that measures or detects a physical property and responds to the property by recording, indicating or transmitting a resultant impulse. Sensors used include both biological and non-biological sensors such as motion sensors and accelerometers as well as active and passive sensors.

"Energy source" as used herein refers to a source from which energy can be extracted or recovered. The energy can be extracted either directly or through conversion or transformation. In some embodiments, the energy source is a radio frequency source.

"Energy" as used herein refers to usable power. There are 3 general categories for energy: radiant energy, thermal energy, and mechanical energy. Radiant energy includes, but is not limited to, solar energy and radio frequency (RF) energy and waves. Thermal energy includes, but is not limited to, external heat and body heat. Mechanical energy includes, but is not limited to, body motion; blood flow; piezoelectric energy; air flow; and vibrations. There are several different types of energy such as electrical, chemical, thermal, mechanical, and nuclear. In some embodiments, the type of energy used is RF energy and waves.

The invention is a novel electronic system for wirelessly powering moving biological sensors without the need of batteries. The system employs energy harvesting technology to continuously deliver a constant power supply to the sensors, which enables long term, accurate data collection.

The instant invention presents an innovative solution that allows for effective energy collection and conversion, regardless of the position of the receiving antenna and its motion dynamics. The invention is intended for use in animal research, however, it can be adapted to work with any sensor and subject that remains within an enclosed space. Energy transmitters are strategically placed around this space to provide the necessary power.

The system consists generally of six components: a plurality of energy transmitters, receiving antenna, energy harvester, energy storage unit, microprocessor and at least one sensor. Most of the components can be adapted for specific purposes according to the type of energy used. For example, the type of sensor (e.g. pressure, temperature, etc.) used in the system would be dependent on the application.

FIG. 1 provides an example schematic of the system. An energy source, such as a radio frequency (RF) source, is placed near the receiver. The system harvests the RF energy and converts it to a DC voltage that is sent to a storage unit. This energy is then used to power a programmable microprocessor, which runs the system in two modes: sleep mode and active mode. During sleep mode the sensors are turned OFF and the microprocessor consumes close to zero current, allowing for storage of all the energy harvested. During active mode, the microprocessor turns on the sensor and records data at the programmed sampling rate. This data is then transmitted out to a receiver that interfaces with a computer for its display and long term storage. A more detailed description of the system components is offered below.

System Components

RF Transmitter:

RF transmitters have two main settings: frequency and emission strength. The transmission frequency used in the system can be adapted to any frequency that is compatible with the harvester. The only restriction is that the harvesting frequency bandwidth must be far apart enough from the data transmission frequency to avoid interference. For example, a harvesting frequency of 915 MHz and a data transmission frequency of 2.4 GHz can be effectively implemented. The required emission strength depends on the amount of energy needed to power the device. Large amounts of energy loss are also expected due to environmental influence in the signal before it reaches the harvester, therefore, large power outputs are recommended.

An RF transmitter creates an energy field in a very specific orientation. In order to maximize the reception of the transmitted energy, the receiving antenna must be aligned with the emitted field. If the receiving antenna is constantly moving randomly, as is the case with biological sensors, this alignment is less than optimal most of the time. A novel solution to this problem was created by placing multiple transmitters in orthogonal orientations within the reach of the receiver. This sets up two equally strong RF fields with a 90-degree difference in orientation. In this fashion, regardless of the subject's position, the receiving antenna will always be aligned with one of the fields. Experiments were conducted using only one transmitter, which resulted in a less strong field and therefore less stable and weaker energy output at the harvester. However, a single transmitter setup may be suitable for low power applications.

Figure 2:
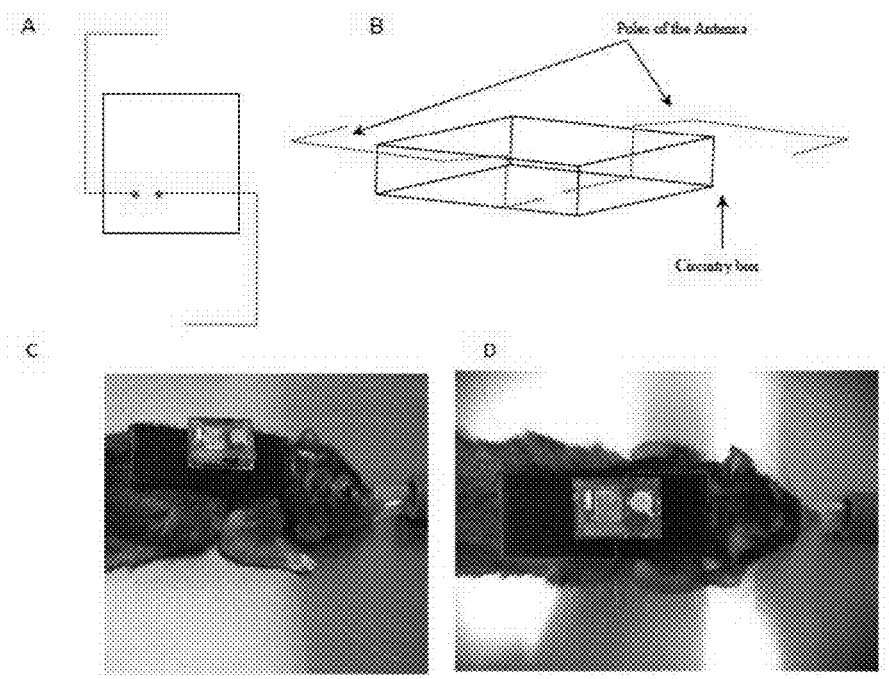
FIG. 2 is a series of images depicting the receiving antenna. (A) Top view of the dipole antenna pattern used to detect RF fields. (B) 3D representation of the antenna pattern and circuitry box case. (C, D) Pictures of rat wearing jacket-system bundle. Dotted Red line depicts the location of the antenna within the vest.

Receiving Antenna:

In an embodiment, the antenna is a dipole wire antenna that is attached to the energy harvester. The length of each of the poles of the antenna is dependent on the frequency used for harvesting. In the case of 915 MHz, each is about 8.2 cm long. The antenna works best when poles are completely straight, directed 180 degrees away from each other and aligned with the RF field. However, the length of the poles creates a challenge for implantation. In most biological applications, an 8.2 cm long straight wire is not suitable to be placed subcutaneously and leaving the wire exposed can lead to unwanted bending of the antenna that could disrupt energy reception or overall damage of the wire. Therefore, a second challenge is presented when the shape of the poles is modified to allow them to fit within the dimensions of the system. In order to secure the antenna to the animal, a custom vest was designed to fit tightly around the back and chest of the animal. An innovative 3D architecture pattern (FIG. 2) was developed to bend the antenna in such a way that it creates maximum alignment of sections of the antenna with the two RF fields being generated by the transmitters, while staying within the confines of the vest. Both poles of the antenna connect to the rest of the circuitry, encased in a small plastic box that attaches firmly to the vest. From there, they are routed out of the box and embedded within the fabric of the vest in order to protect it from contact and maintain the original shape. Other antenna patterns are possible, however the one presented here generated outstanding results.

Harvester:

The RF energy harvester operates in a wide range of frequencies (about 60 Hz to about 6 GHz) allowing for multiple options of RF transmission frequency. The output of the harvester runs through a Schottky diode to prevent energy from flowing from the storage unit into the harvester.

Figure 3:
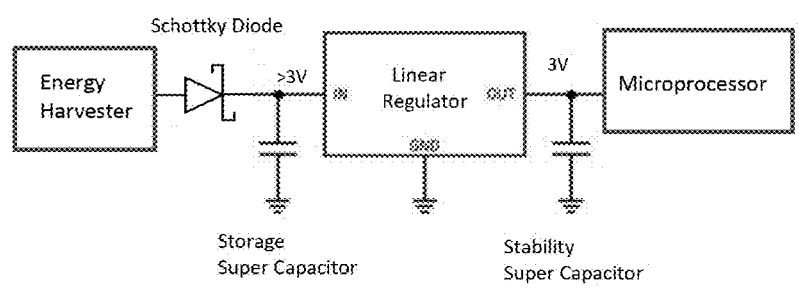
FIG. 3 is an image depicting electronic schematics of the energy storage unit. Two supercapacitors and a voltage regulator are employed to collect energy harvested during sleep mode and deliver steady power supply to the rest of the system during active mode.

Energy Storage Unit:

The energy storage unit consists of at least one supercapacitor and a linear voltage regulator. In an embodiment, 2 supercapacitors and a linear voltage regulator comprise the energy storage unit. FIG. 3 presents the electronic schematic of this unit. The first supercapacitor serves to store most of the energy generated by the harvester so that it is available for the active cycle of the system. In order to ensure that the microprocessor is not exposed to a supply voltage greater that it can handle (e.g. 3V), the first supercapacitor is connected to the linear voltage regulator, which converts any input greater than 3V into exactly 3V and outputs the power to the microprocessor. The second supercapacitor serves for stability, eliminating output noise due to fluctuations in the first capacitor. If at any point the first capacitor falls below 3V, the second capacitor acts as a supplemental energy supply that maintains power to the microprocessor while the main capacitor recharges.

Microprocessor:

The microprocessor is programmed to run the sleep and active modes. It features multiple general purpose channels that can be configured as input or output channels. During the sleep cycle, virtually all the harvested energy is stored. During the active mode the output channels are used to provide supply power to the sensor(s) and the input channels are used to collect the data coming from such sensor(s). The microprocessor stores the data in its memory before transmission. In order to maximize the recharge ability of the system, its power consuming features are split in two: data collection and data transmission. Therefore, the system is run in a 4 step cycle: sleep mode/data collection/sleep mode/data transmission. This configuration avoids large energy consumption at once, which could produce a large drop in the energy stored and cause the system to fall below the minimum operating voltage level. The cycle time is configurable and depends on the amount of energy that the system consumes per cycle. (e.g. systems that require more energy during each cycle will require longer cycle times that create longer sleep mode times, allowing the system to recharge the energy used). The microprocessor is equipped with a built-in ultra-low power Bluetooth transmitter and 2.4 GHz antenna that can send data to the receiver. The receiver consists of a second identical microprocessor that communicates with the transmitter and downloads the data to a computer for display and analysis. Multiple transmitters can be used simultaneously with a single receiver.

Sensor:

Any sensor that operates with a power supply compatible with the microprocessor's supply can be used with the system. The system is equipped with an amplifier that allows for amplification of the signal before transmission, which assures the best possible data resolution.

Metal Shielding:

A reflective metal cage may be incorporated as a seventh component to improve energy harvesting for applications that experience significant transmission loss. Energy transmission is governed by Friis equation:

$$P_r = P_t G_t G_r \lambda^2 / (4\pi R)^2$$

Where $P_r$ is the power received, $P_t$ is the power transmitter, Gt and Gr are the gains of the transmitter and receiver antennas, $\lambda$ is the wavelength and R the distance between the transmitter and receiver. Therefore, the power received drops exponentially as the distance between the antennas is increased. A solution to this problem is to place highly reflective material (e.g. aluminum, copper, etc.) in the surroundings of the device so as to redirect the energy that would otherwise be lost into the environment towards the receiver. For example, in animal research applications, the animal is confined to a cage that can be easily shielded for reflection. Energy can then be redirected to create a stronger field within the confinement of the animal's cage, which could help in high power demanding applications.

Power Cycling:

The system is run in a power cycle with two modalities. First is the active mode, during which data is collected from the sensor and transmitted wirelessly to a computer for analysis and display. The second modality is the sleep mode, in which all sensors are turned OFF and the microprocessor consumes minimal current. This allows all energy harvested during the sleep mode to be stored in the system's energy storage unit.

In order for the system to operate optimally, the voltage stored in the supercapacitors must be maintained between the minimum and maximum operating levels. The lower threshold is established by the minimum supply voltage that the microprocessors requires to work. (e.g. 3V). On the other hand, the supercapacitor's voltage ratings determine the maximum voltage level that can be stored. Higher voltage ratings can be achieved with larger supercapacitors and are only limited by size restrictions of a particular application.

In order to avoid large drops in stored power, which could cause the stored voltage to fall below the minimum threshold, power consuming features of the active modality (data collection and data transmission) are done separately. The power cycle is then run in four steps: data collection/sleep mode/data transmission/sleep mode. By incorporating a sleep mode period in between collection and transmission, power drops are split into two smaller events, with a period in the middle in which the system is able to recharge the energy that was just consumed. The length of each one of the sleep modality steps is completely customizable and can be adapted to specific applications. For example, applications that consume large amounts of energy during collection or transmission of data will require a longer sleep period in order to recharge that energy. On the other hand, applications with lower power consumption on each one of these steps can be implemented with very short sleep periods, allowing for more frequent sampling rates and more data points to be collected.

Figure 7A:
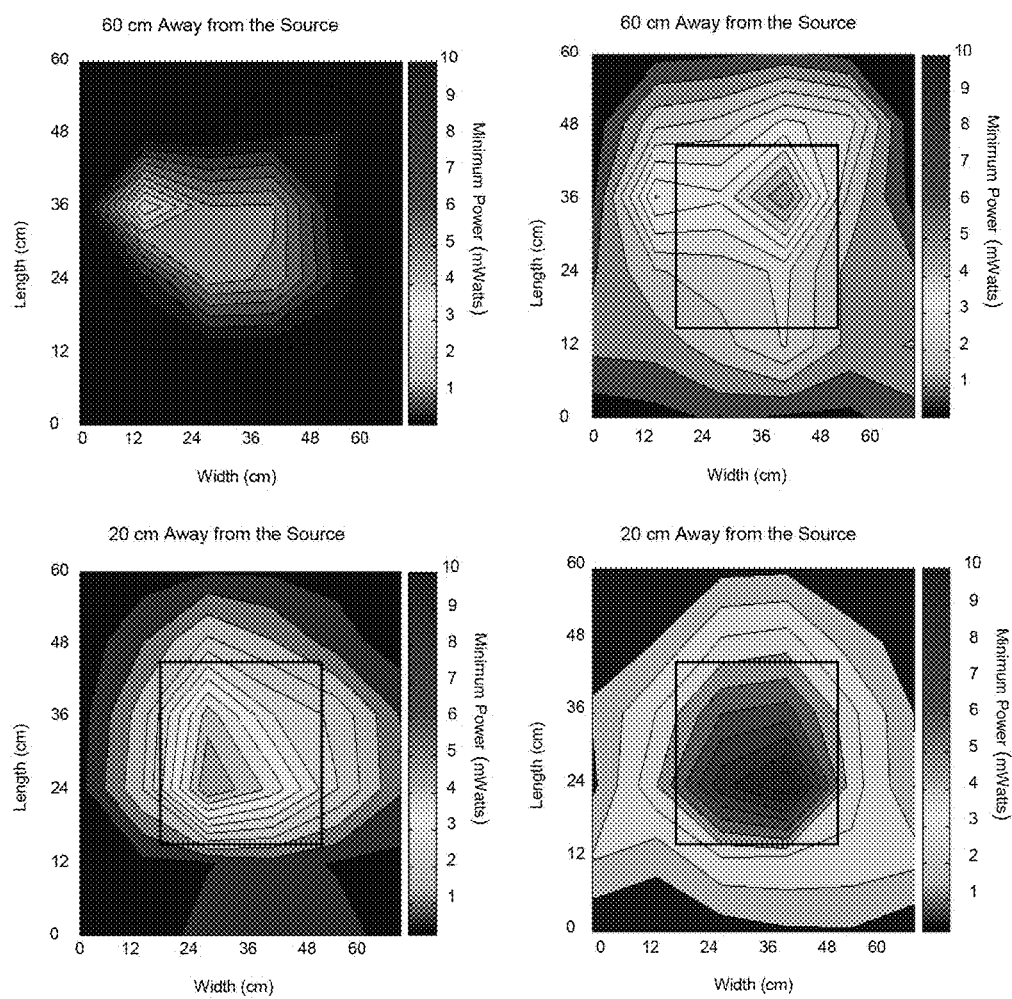
FIG. 7A is a series of graphs depicting RF-DC mapping around the cage with system on a fully awake rat. Receiving antenna's power reception inside and around the cage (the cage is represented by the square) at 20 cm and 60 cm from the transmitter.
Figure 7B:
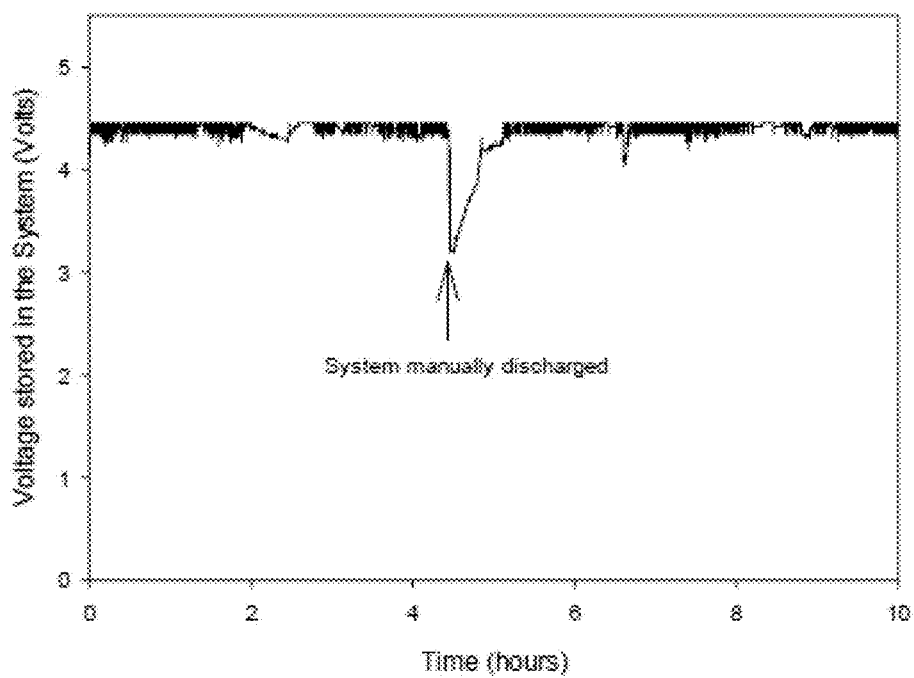
FIG. 7B is an image depicting voltage stored in the system during 10 hours of operation. The system was mounted on a fully awake rat. During most of the experiment, voltage levels were kept close to the upper 4.5V threshold. At this level, data is sampled continuously at 300 Hz. Between hours 4 and 5, the system was manually discharged to test the ability of the system to recover and power itself after a sudden energy drain. The device successfully recharged and returned to the upper threshold within an hour.
Figure 8C:
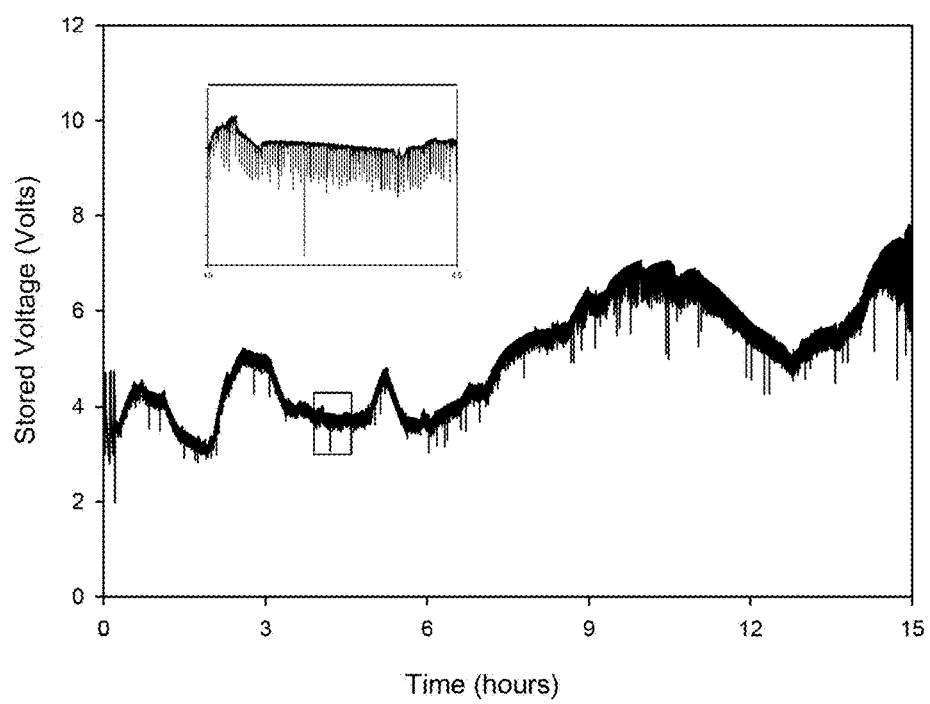
FIG. 8C is a series of images depicting hydrostatic pressure measurement and recharge cycle with the system mounted on a rat. C) Voltage stores in the system over 15 hours (outer) showing that energy harvested is greater than the energy consumed. The close up from hours 4 to 4.5 (inner) shows periodic power consumption due to system cycling between active and sleep mode.
Figure 9:
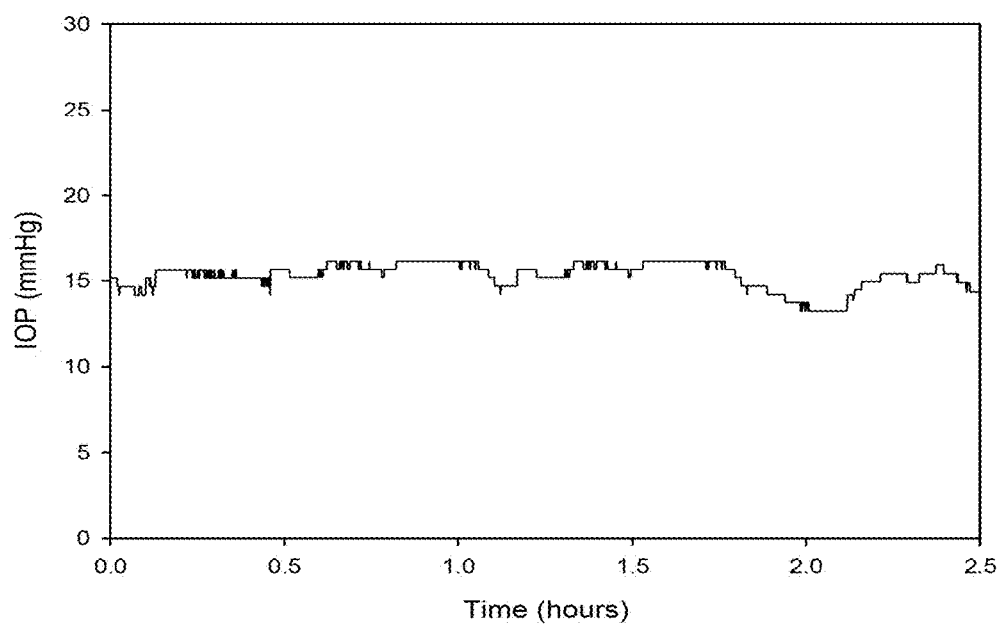
FIG. 9 is a graph depicting TOP measurement in anesthetized rats. The graph shows intraocular pressure monitoring of a rat under ketamine anesthesia using the device.

The system can also be operated in a smart power cycle, in which the data sampling rate is automatically adapted depending on the amount of energy available. For instance, when the system has low energy stored and available for use, the sampling frequency decreases in order to avoid dropping below the minimum operating levels. This decrease in the data sampling frequency, also decreases energy consumption and allows the system to increase the energy storage levels. Conversely, as these levels rise, the sampling rate returns to the normal pre-set sampling value, which is set based on the application. When energy levels reach the higher threshold of operation, the system adapts the sampling rate once again, this time increasing it and allowing the user to obtain continuous data sampled at several hundred Hertz for several seconds. FIG. 7B illustrates the performance of the system using the smart power cycle and the antenna design illustrated in FIG. 2. Through 10 hours of operation, the system maintained the voltage stored in the system between the operating levels (3-4.5V). In fact, during most of the experiment, voltage levels were kept close to the upper threshold, ensuring that most data was obtained continuously while sampling at 300 Hz.

Application in Animal Research

Animal research is one of the most important tools for disease and drug treatment research. A significant part of that research is done with implantable devices, in which different sensors are embedded in the animal in order to continuously monitor the parameter of interest. Most of these devices are battery powered, which presents a significant limitation for two main reasons: battery-dependent calibration and lifetime of the device.

First, as batteries start to drain, the power supplied to the sensors starts to decay, affecting the ability of the sensor to respond to a stimulus. This requires the sensors to be constantly recalibrated in order to obtain accurate readings. Since the devices are surgically connected to the animal, researchers cannot simply remove the sensor in order to perform the recalibration. Therefore, the animal subject must undergo additional procedures for recalibration purposes. This not only means extra work for the researcher, but could also compromise the health of the animal and the organ that is being studied.

Secondly, the lifetime of the battery limits the operational time of the device. Many studies require the implanted devices to work for months at a time in order to obtain adequate and significant data. Thus, a short battery life will significantly limit the success of such studies. The use of longer-lasting batteries is often untenable due to size restrictions. In an effort to maximize battery life, researchers usually compromise resolution and accuracy of the collected data, as well as limit the features that a single device can offer. For example, a device that is not equipped with an amplifier can save power by transmitting data directly from the sensor but the accuracy of that data would be inadequate for most applications.

The proposed invention is a novel system that allows implantable sensors to be continuously powered without the need of batteries. The system allows for virtually unlimited battery life, without any recalibration being necessary and provides maximum resolution for the data obtained. Additionally, the system does not restrict movement of the subject, allowing it to go through its daily motions without affecting the performance of the system. In the past, energy harvesting has been used for other applications, with the receiver remaining in a fixed position in them all.

Figure 4:
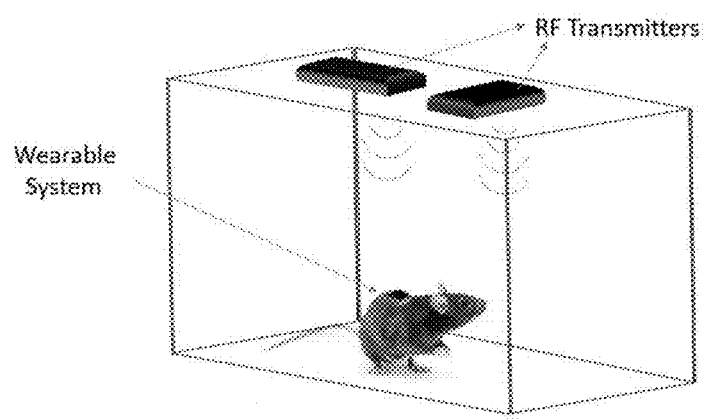
FIG. 4 is an image depicting schematics of wirelessly powering device used on a rat for glaucoma studies. Two RF transmitters were placed orthogonally on top of the rat's cage in order to create a multi-directional RF field for energy harvesting.
Figure 5:
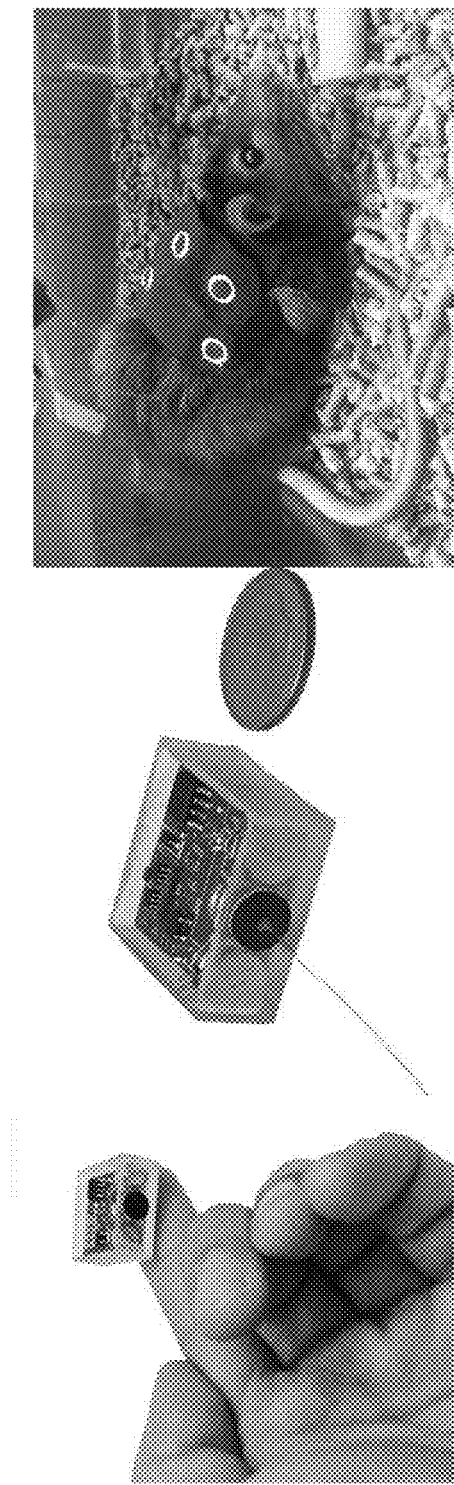
FIG. 5 is a series of images depicting the implantable wireless TOP sensor.
Figure 6:
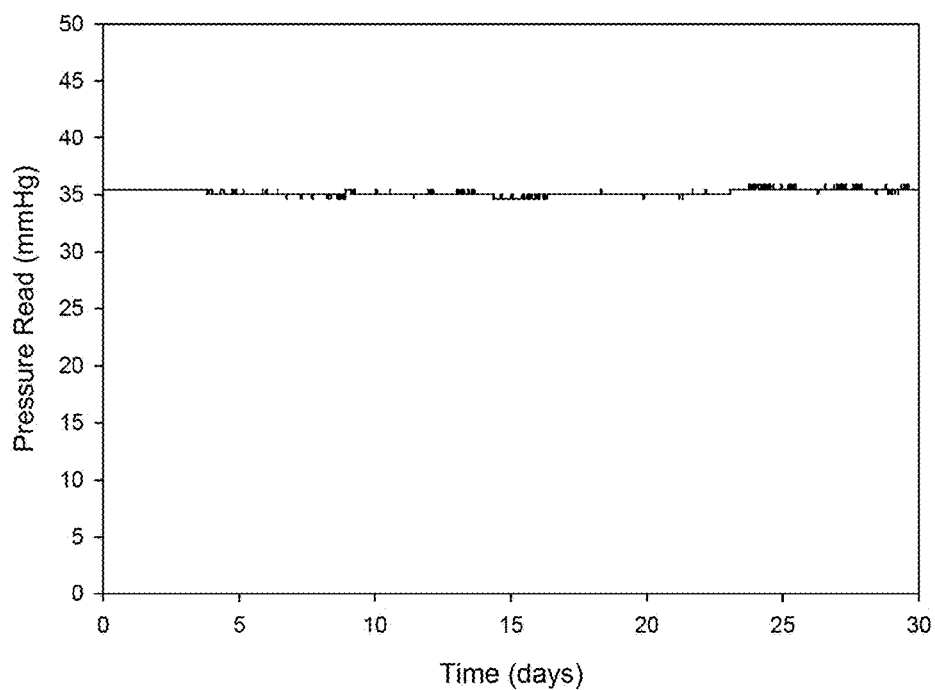
FIG. 6 is a graph of the pressure sensor under 35 mmHg of constant hydrostatic pressure. After one month the sensor experienced no drift in its measurements.

A prototype was built to measure intraocular pressure of a rat in order to study glaucoma. FIG. 4 presents schematics of this instantiation of the device. Two 915 MHz RF transmitters were placed on top of the rat's cage which created two RF fields (one along the length and the other one along the width of the cage). The rat wore a customized backpack that enclosed a 20×25 mm box containing the antenna, harvester, energy storage unit, microprocessor and a miniature pressure sensor. The system accurately recorded and transmitted pressure signals every second over several hours. Voltage levels stored in the capacitor were monitored and found to not only stay well above the minimum levels, but to increase over time, which indicates that the amount of energy harvested was much greater than that being consumed by the system.

The invention is not limited to sensors but also applies to more power consuming devices like a fluidic pump or current stimulator. The multiple data channels available in the device allow for the incorporation of numerous features that can be run simultaneously in order to create more comprehensive research studies. Other features that are capable of being powered by the device include, but are not limited to, chronic drug delivery capabilities; electrical stimulation of an organ (e.g. ocular stimulation for electroretinogram recordings); applications that require micropumps and miniature controllers to deliver specific doses of a drug to a target organ, etc. Similarly, electrical stimulation of an organ can be achieved by using the device to modulate the amplitude of a current or voltage wave delivered through an electrode or wire. Overall, any electronic system that is small enough for implantation can be potentially powered using this technology.

Application to Power Moving Sensors in Large Buildings

The invention also has potential applications beyond biological sensing in animals. The idea can be adapted to continuously power multiple moving sensors in large buildings. For example, in hospital settings where patients' vital signs need to be continuously monitored, the invention could be implemented to record a patient's vitals while allowing them to move around the hospital. This way, if the patients need to leave their bed, they can do so freely and the hospital staff will still be able to monitor their vital signs wirelessly. Transmitters could be mounted in the walls to create multidirectional RF fields that could allow patients to move throughout the hospital without fear of power loss to sensors on their body. Similarly, other non-biological sensors (e.g. motion sensors, accelerometers, etc.) could also be worn and wirelessly powered using this technology. This could facilitate data acquisition of such parameters during sporting events or training facilities to obtain statistical information of a person's speed, strength, among others, while wearing minimum equipment.

Application in Recharging Electronic Devices Using Batteries

The invention can also be adapted for recharging electronic devices that use batteries. Unlike cell phone charging mats, where the charging device must be place on top of the mat and cannot be removed, the invention would allow the user to move freely across a room that has an RF transmission device set up as described in FIG. 1 and recharge their electronics as they do so. This could be done in an office or a house, or perhaps in airports, schools and sport arenas as well. For example, many travelers would like to recharge their electronics while they wait to catch a flight, but cannot because outlets and recharging stations are limited in number in the airport. Setting up multiple transmission units across the terminal would allow people to walk freely and recharge their devices at the same time.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually. Furthermore, where a definition or use of a term in a reference, which is incorporated by reference herein, is inconsistent or contrary to the definition of that term provided herein, the definition of that term provided herein applies and the definition of that term in the reference does not apply.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

While there has been described and illustrated specific embodiments of the invention, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween.

What is claimed is:

1. A system for continuous wireless powering comprising:
    an RF energy harvester;
    a receiving antennae oriented in a three dimensional configuration attached to the RF energy harvester;
    at least one RF transmitter positioned around the receiving antennae;
    an energy storage unit connected to the RF energy harvester wherein the energy storage unit is comprised of at least two supercapacitors and a linear voltage regulator;
    a microprocessor connected to the energy storage unit; and
    at least one sensor connected to the microprocessor;
    wherein the microprocessor transmits data collected from the at least one sensor to a computer which stores and presents the data.

2. The system of claim 1, further comprising highly reflective material positioned around an area in which the system operates.

3. The system of claim 1, wherein voltage stored in the at least two supercapacitors is maintained between minimum and maximum operating levels.

4. The system of claim 1, wherein the at least one sensor is a biological sensor implanted in a moving subject.

5. The system of claim 1, wherein there are at least two RF transmitters.

6. The system of claim 5, wherein the at least two RF transmitters are positioned around the receiving antennae in an orthogonal orientation.

7. The system of claim 1, wherein a plurality of RF transmitters are positioned around the receiving antenna to create multidirectional RF fields.

8. The system of claim 1, wherein the microprocessor is comprised of multiple general purpose channels capable of being configured as input or output channels.

9. The system of claim 1, wherein the system is run in an active mode and a sleep mode.

10. The system of claim 1, wherein energy output from the energy harvester is run through a Schottky diode.

11. The system of claim 1, wherein the receiving antenna is a dipole wire antenna.

12. A method of continuous wireless powering of a device comprising:
    providing a system for continuous wireless powering comprising:
        an energy harvester having a receiving antennae oriented in a three dimensional configuration
        at least one RF transmitter positioned around the receiving antennae;
        an energy storage unit connected to the RF energy harvester wherein the energy storage unit is comprised of at least two supercapacitors and a linear voltage regulator;
        a microprocessor connected to the energy storage unit; and
        at least one sensor connected to the microprocessor;
    running the system by power cycling through two modalities wherein the two modalities are a sleep mode and an active mode; and
    transmitting data to a computer.

13. The method of claim 12, further comprising positioning highly reflective material around an area in which the system operates.

14. The method of claim 12, wherein the device being powered is at least one sensor.

15. The method of claim 14, wherein the at least one sensor is a biological sensor attached to a moving subject.

16. The method of claim 12, wherein there are at least two RF transmitters.

17. The method of claim 16, wherein the at least two RF transmitters are positioned around the receiving antennae in an orthogonal orientation.

18. The method of claim 12, wherein the receiving antenna is a dipole wire antenna.

* * * * *